United States Patent [19]
Shen et al.

[11] Patent Number: 6,018,031
[45] Date of Patent: *Jan. 25, 2000

[54] BINDING AGENTS SPECIFIC FOR IGA RECEPTOR

[75] Inventors: Lilian Shen, Thetford Center, Vt.; Michael W. Fanger, Lebanon, N.H.

[73] Assignee: Trustees of Dartmouth College, Hanover, N.H.

[*] Notice: This patent is subject to a terminal disclaimer.

[21] Appl. No.: 08/756,142

[22] Filed: Nov. 26, 1996

Related U.S. Application Data

[63] Continuation-in-part of application No. 08/222,572, Apr. 4, 1994, Pat. No. 5,610,057, which is a continuation of application No. 07/871,561, Apr. 16, 1992, abandoned, which is a continuation of application No. 07/424,883, Oct. 20, 1989, abandoned.

[51] Int. Cl.⁷ .............................. C12P 21/08; C07K 16/00
[52] U.S. Cl. ..................... 530/387.3; 530/387.7; 530/388.2; 530/388.22
[58] Field of Search ............................. 530/387.3, 388.2, 530/388.8, 388.22, 387.7, 388.1, 388.3, 388.35, 388.4, 388.6, 388.73, 388.85, 389.1; 435/240.27, 70.21, 172.2; 424/136.1, 141.1, 154.1, 155.1, 174.1

[56] References Cited

U.S. PATENT DOCUMENTS

| | | | |
|---|---|---|---|
| 4,816,567 | 3/1989 | Cabilly et al. | 530/387 |
| 5,001,225 | 3/1991 | Taylor | 530/387 |
| 5,610,057 | 3/1997 | Shen et al. | 435/334 |
| 5,635,600 | 6/1997 | Fanger et al. | 530/387.3 |

FOREIGN PATENT DOCUMENTS

| | | |
|---|---|---|
| 0 255 249 | 2/1988 | European Pat. Off. . |
| WO 91/00360 | 1/1991 | WIPO . |
| WO 91/05805 | 5/1991 | WIPO . |
| WO 92/05793 | 4/1992 | WIPO . |
| WO 94/08038 | 4/1994 | WIPO . |
| WO 95/16037 | 6/1995 | WIPO . |
| WO 95/24220 | 9/1995 | WIPO . |
| WO 9802463 | 1/1998 | WIPO . |

OTHER PUBLICATIONS

Adachi et al (J. Immunol., 1983, 131:1246–1251).
Segal et al (Princess Takamatsu Symposium, 1988, 19:323–331, Abstract enclosed.
Maliszewski et al (J. Immunol, 1985, 135:3878–3881).
Queen et al (PNAS, 86: 10029–10033, 1989).
Queen et al (PNAS, 86:10029–10033), 1988.
Huston et al (PNAS, 85:5879–5883), 1988.
Tokomoto et al (Monogr. Allergy, 24:208–214), 1988.
Albrechtsen et al (Immunology, 64:201–205), 1988.
Montiero et al (Faseb J., 3:A110), 1989.
Johnstone and Thorpe (Immunochemistry in Practice, 2nd Ed., Blackwell Scientific Publications, Oxford, p. 30, 1987.

Morton et al. "Purification and Characterization of Chimeric Human IgA1 and IgA2 Expressed in COS and Chinese Hamster Ovary Cells" *The Journal of Immunology* 151(9):4743–4752 (1993).

Morton et al. "Structure and Function of Human IgA Fc Receptors" *Critical Reviews in Immunology* 16:423–440 (1996).

Shen, Li "A monoclonal Antibody Specific for Immunoglobulin A Receptor Triggers Polymorphonuclear Superoxide Release" *Journal of Leucocyte Biology* 51(4):373–378 (1992).

Alkan, S. et al., "Enhanced Antiproliferative Action of Interferon Targeted by Bispecific Monoclonal Antibodies," *Journal of Interferon Research*, vol. 8, 25–33 (1988).

Bacus, S. et al., "Expression of the erbB–2 Family of Growth Factor Receptors and their Ligands in Breast Cancers," *Am J Clin Pathol*, vol. 102, supp. 1, S13–S24 (1994).

Bajorath, J. and Sheriff, S., "Comparison of an Antibody Model with an X–Ray Structure: The Variable Fragment of BR96," *Proteins: Structure, Function, and Genetics*, vol. 24, 152–157 (1996).

De Potter, C. and Schelfhout, A., "The Neu–Protein and Breast Cancer," *Virchows Archiv*, vol. 426, 107–115 (1995).

Devilee, P. et al., "Recent Developments in the Molecular Genetic Understanding of Breast Cancer," *Critical Reviews in Oncogenesis*, vol. 5, No. 2 & 3, 247–270 (1994).

Earp, H. et al., "Heterodimerization and Functional Interaction Between EGF Receptor Family Members: A New Signaling Paradigm with Implications for Breast Cancer Research," *Breast Cancer Research and Treatment*, vol. 35, 115–132 (1995).

Grossetête, B. et al., "Impaired Fcα Receptor Expression is Linked to Increased Immunoglobulin A Levels and Disease Progression in HIV–1–Infected Patients," *AIDS*, vol. 9, 229–234 (1995).

Harris et al., "Therapeutic Antibodies—The Coming of Age," *TIBTECH*, vol. 11, 42–44 (1993).

Jardines, L. et al., "neu(c–erbB–2/HER2) and the Epidermal Growth Factor Receptor (EGFR) in Breast Cancer," *Pathobiology*, vol. 61, 268–282 (1993).

(List continued on next page.)

*Primary Examiner*—Paula K. Hutzell
*Assistant Examiner*—Susan Ungar
*Attorney, Agent, or Firm*—Lahive & Cockfield, LLP; Jane E. Remillard; Giulio A. DeConti, Jr

[57] ABSTRACT

Binding agents which bind specifically to a receptor for human IgA, including monoclonal antibodies which react specifically to Fc receptor for IgA of human effector cells are disclosed. The binding agents, e.g., antibodies are useful for targeting human effector cells (e.g. macrophages) against a target cell (e.g. a cancer cell, an infectious agent, etc.). For this purpose, bifunctional antibodies or heteroantibodies can be constructed containing the binding region derived from an anti-Fc-alpha receptor antibody and the binding region of a target-specific antibody. Targeted effector cells can specifically lyse target cells.

9 Claims, No Drawings

OTHER PUBLICATIONS

Johnson, G. et al., "Seqhunt: A Program to Screen Aligned Nucleotide and Amino Acid Sequences," *Methods in Molecular Biology*, vol. 51, ch. 1, 1–15 (1995).

Keler, T. et al., "Bispecific Antibody (MDX–210) Targeting of Tumor Cells to Monocytes Via the Fc Receptor Type I (FcγRI) Promotes Antibody Dependent Cellular Cytotoxicity (ADCC) and Induction of Specific Cytokines," *Proceedings of the American Association for Cancer Research*, vol. 36, 485 (1995).

Kubagawa, H. et al., "Cloning of Genes Encoding Possible Murine Fcα Receptors (FcαR)," *FASEB J.*, vol. 8, No. 4–5, A749 (1994).

Mezzanzanica, D. et al., "Human Ovarian Carcinoma Lysis by Cytotoxic T Cells Targeted by Bispecific Monoclonal Antibodies: Analysis of the Antibody Components," *Int. J. Cancer*, vol. 41, 609–615 (1988).

Monteiro, R. et al., "Definition of Immunoglobulin A Receptors on Eosinophils and their Enhanced Expression in Allergic Individuals," *J. Clin. Invest.*, vol. 92, 1681–1685 (1993).

Monteiro, R. et al., "Molecular Heterogeneity of Fcα Receptors Detected by Receptor–Specific Monoclonal Antibodies," *The Journal of Immunology*, vol. 148, No. 6, 1764–1770 (1992).

Patry, C. et al., "Fcα Receptors Mediate Release of Tumor Necrosis Factor–α and Interleukin–6 by Human Monocytes Following Receptor Aggregation," *Immunology*, vol. 86, 1–5 (1995).

Patry, C. et al., "Identification of Fcα Receptor (CD89) Isoforms Generated by Alternative Splicing that are Differentially Expressed Between Blood Monocytes and Alveolar Macrophages," *The Journal of Immunology*, vol. 156, 4442–4448 (1996).

Pfefferkorn, L. and Yeaman, G., "Association of IgA–Fc Receptors (FcαR) with FcεRIγ2 Subunits in U937 Cells," *The Journal of Immunology*, vol. 153, 3228–3236 (1994).

Shen, L., "Receptors for IgA on Phagocytic Cells," *Immunol. Res.*, vol. 11, 273–282 (1992).

Shen, L. et al., "My 43, A Monoclonal Antibody That Reacts with Human Myeloid Cells Inhibits Monocyte IgA Binding and Triggers Function," *Journal of Immunology*, vol. 143, No. 12, 4117–4122 (1989).

Shimada, T. et al., "Comparative Analysis of FcαR on Neutrophils and Monocytes," *FASEB J.*, vol. 9, No. 4, A804 (1995).

Shimo, K. et al., "Ligand–Binding Properties of Recombinant Soluble Fcα Receptor," *FASEB J.*, vol. 9, No. 4, A774 (1995).

Threlkeld, S.C. et al., "Differential Down–Modulation of IgA Fc Receptors (FcαR) on Neutrophils and Monocytes in HIV–Infected and Normal Individuals," *FASEB J.*, vol. 8, No. 4–5, A492 (1994).

Valone, F. et al., "Phase Ia/Ib Trial of Bispecific Antibody MDX–210 in Patients with Advanced Breast or Ovarian Cancer that Overexpresses the Proto–Oncogene HER–2/neu," *J Clin Oncol*, vol. 13, No. 9, 2281–2292 (1995).

Valone, F.H. et al., "Schedule Dependent Immunological Stimulation by Bispecific Antibody (BsAb) MDX–210 (anti–FcγRI x anti–HER–2/neu) in Patients with Breast or Ovarian Cancers that Over Express HER–2/neu," *Proceedings of the American Association for Cancer Research*, vol. 36, 500 (1995).

Webster, D. and Rees, A., "Molecular Modeling of Antibody–Combining Sites," *Methods in Molecular Biology*, vol. 51, 17–49 (1995).

Weisbart, R.H. et al., "GM–CSF Induces Human Neutrophil IgA–Mediated Phagocytosis by an IgA Fc Receptor Activation Mechanism," *Nature*, vol. 332, 647–648 (1988).

Yeaman, G. and Pfefferkorn, L.C., "IgA–Fc Receptors (FcαR) on U937 Cells Associate with FcεRI Gamma Subunits," *FASEB J.*, vol. 8, No. 4–5, A981 (1994).

BINDING AGENTS SPECIFIC FOR IGA RECEPTOR

RELATED APPLICATIONS

This application is a continuation-in-part of U.S. application Ser. No. 08/222,572 filed Apr. 4, 1994 now U.S. Pat. No. 5,610,057 issued on Mar. 11, 1997, entitled "Monoclonal Antibody Specific For IgA Receptor", which is a continuation application of U.S. application Ser. No. 07/871,561 filed Apr. 16, 1992, now abandoned which is a continuation application of U.S. application Ser. No. 07/424,883 filed Oct. 20, 1989, now abandoned. The contents of each of these applications is incorporated herein by reference.

BACKGROUND

Receptors for the Fc portion of immunoglobulin are important in triggering many of the protective functions of monocytes, macrophages and polymorphonuclear cells. While receptors for IgG on these cells have been extensively investigated, it is becoming evident that receptors for IgA are also capable of promoting effector functions of these cells and that IgE may stimulate some activities of monocytes. While soluble IgA binds IgA receptor with poor avidity, polymerized IgA has been demonstrated to trigger functions such as superoxide generation and phagocytosis.

SUMMARY OF THE INVENTION

This invention pertains to a binding agent having at least one antigen binding region specific for a receptor for IgA, e.g., Fc$\alpha$R (CD89). The binding agent of the invention preferably triggers an Fc receptor-mediated effector cell activity, such as phagocytosis or secretion of superoxide anion upon binding to the receptor on an effector cell. In a preferred embodiment, binding of the binding agent to the Fc$\alpha$R is not inhibited by IgA. Accordingly, the binding agent preferably binds an Fc$\alpha$R at a site different from the IgA binding site.

The binding agent can be a monospecific binding agent or the binding agent can be a multispecific or heterospecific binding agent, such as a bispecific binding agent. Multispecific binding agents are useful for linking an effector cell to a target antigen, such as an epitope on a tumor cell, an autoantibody producing cell, a pathogen infected cell, or any other undesirable cell, thereby resulting in cytolysis of the cell having the target antigen or in phagocytosis of the target antigen. Other target antigens include soluble antigens or complexes of antigens, and microorganisms, e.g, viruses and bacteria In one embodiment, the binding agent is a monoclonal antibody which specifically binds to Fc receptors for IgA (Fc-alpha receptor) on effector cells such as a monocytes, polymorphonuclear cells and macrophages and which can trigger Fc-alpha-receptor-mediated effector function. The antibody (or fragment thereof) can be linked (chemically or genetically) to an antibody (or fragment thereof) specific for a target antigen to form a bispecific antibody or heteroantibody. These bispecific molecules can be used to direct effector cells to cell bearing the target antigen, resulting in cytolysis of the target cell.

The invention also pertains to methods using a binding agent having at least one antigen binding region specific for an Fc$\alpha$R. In a specific embodiment, a binding agent is administered to a subject having, e.g., a cancer, an autoimmune disease, a pathogenic infection, or an allergy. Alternatively, the invention provides methods for ex vivo use of binding agents for treating such disorders.

Based on their ability to bind Fc$\alpha$R bearing immune cells and specific target cells, in a particular embodiment of the invention, a binding agent is administered to a subject to treat or prevent reoccurrence of a variety of diseases or conditions, including: cancer (e.g., breast, ovarian, testicular, prostate, lung, brain, colon, rectum, pancreas, liver, central nervous system, head and neck, kidney, bone, blood and lymphatic system), pathogenic infections such as viral (such as HIV, HTLV and FELV), protozoan (such as *Toxoplasma gondii*), fungal (such as *Candida albicans*); and bacterial (such as *Staphylococcus aureus, Streptococcus hemolyticus* and *Mycobacterium tuberculosis*). Another aspect of the invention provides molecules that are useful for vaccination against diseases and cancer by including an antigen from disease organisms, from infected cells, from gene products of disease organisms or from cancer cells. For these purposes, the invention provides compositions which are binding agents that link the useful operative antigen to a binding determinant that directs the antigen to the immune system.

Also within the scope of the invention are nucleic acids encoding binding agents, expression vectors comprising such nucleic acids, and host cells containing such. A host cell can be, for example, a hybridoma producing a monoclonal antibody specific for an Fc$\alpha$R.

Further within the scope of the invention are kits containing at least one binding agent specific for an Fc$\alpha$R and instructions for use.

Other features and advantages of the present invention will become better understood by reference to the following Detailed Description and Claims.

DETAILED DESCRIPTION OF THE INVENTION

The invention pertains to a binding agent having at least one antigen binding region specific for an IgA receptor, e.g., a human IgA receptor. In a preferred embodiment of the invention, binding of the binding agent to an IgA receptor triggers Fc receptor mediated effector cell activity. In an even more preferred embodiment of the invention, binding of the binding agent to an IgA receptor is not inhibited by binding of IgA to the receptor. The antigen binding region can be, e.g., from an antibody.

The term "antigen binding region" used interchangeably herein with the term "antigen binding site" is intended to include a region of an agent, such as a protein or a peptide, or derivative thereof, which specifically binds to an antigen. Binding specifically to an antigen is intended to include binding to the antigen which significantly higher affinity than binding to any other antigen. Accordingly, the term "binding specifically" is used herein as defined in the art. The terms "a binding agent recognizing an antigen" and "a binding agent specific for an antigen" are used interchangeably herein with the term "a binding agent which binds to an antigen".

The invention pertains to binding agents having at least one antigen binding region specific for an IgA receptor. In one embodiment, the IgA receptor is an Fc-alpha receptor (Fc$\alpha$R), such as an Fc$\alpha$R for human IgA. Fc$\alpha$Rs are present on monocytes, macrophages, neutrophils, and other myeloid cells. Fc$\alpha$Rs can also be found on metamyelocytes, myelocytes, promyelcytes and some myeloblasts from , e.g., bone marrow. Such receptors can also be found on myeloid cell lines, e.g., U937, PLB985, and HL60 cells. It has also been suggested that Fc$\alpha$Rs are present on lymphocytes. Expression of Fc$\alpha$Rs can be increased by activation of myeloid cells. For example, stimulation of U937 cells and PLB985 cells with Phorbol Myristic Acetate (PMA) increases the cell surface level of FcαR several folds (Maliszewski, et al. (1990) *J. Exp. Med.* 172:1665). Other agents which can increase the surface level of FcαRs include calcitriol, 1–25 dihydroxyvitamin D3, and interferon-γ (IFN-γ).

FcαRs are capable of interacting with IgA1 and IgA2, in the form of monomers, dimers, and polymers. Binding of IgA to cells bearing these receptors induces a variety of effector functions, such as phagocytosis, antibody dependent cellular cytotoxicity (ADCC), inflammatory mediator release, lysozyme production, and superoxide anion production (Maliszewski, et al. (1990) *J. Exp. Med.* 172:1665). Accordingly, preferred binding agents of the invention are binding agents which are capable of triggering at least one Fc-receptor mediated effector cell function. The term "Fc-receptor mediated effector cell function" is intended to include effector functions, such as those set forth above, which are triggered by binding of immunoglobulin, e.g., IgA, to an Fc receptor on an effector cell.

An effector cell is a cell which is involved in the effector phase of an immune response, as opposed to the cognitive and activation phases of an immune response. Effector cells include lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. An effector cell can phagocytose a target antigen, target cell, or microorganism. An effector cell can also lyse a target cell or a microorganism.

In one embodiment of the invention, the binding agent has an antigen binding region similar to an antigen binding region from a monoclonal antibody specific for human FcαR which is capable of triggering Fc receptor mediated effector cell function. For example, monoclonal antibody My 43 (ATCC Accession No. HB 12128) has been shown to trigger effector cell function, e.g., superoxide anion secretion, upon binding to an FcαR. Accordingly, in one embodiment of the invention, the binding agent has an antigen binding region which is similar to the antigen binding region of monoclonal antibody My 43 having ATCC Accession No. HB 12128. The phrase "antigen binding region similar to that of a specific antibody" is intended to include antigen binding regions which are substantially similar in amino acid sequence to that of an antigen binding region from a specific antibody. Accordingly, such antigen binding regions include those deriving from an antibody recognizing a specific antigen, e.g., FcαR, which have been mutated by deletion, addition, or substitution of at least one amino acid. Binding of such binding agents to their target antigen can be confirmed by binding experiments well known in the art, such as flow cytometry or ELISA. In another embodiment of the invention, the antigen binding region of the binding agent specifically binds to an epitope to which monoclonal antibody My 43 (ATCC Accession No. HB 12128) binds. In yet a further embodiment of the invention, the antigen binding region of the binding agent is from monoclonal antibody My 43 (ATCC Accession No. HB 12128).

In a preferred embodiment of the invention, binding of the binding agent to an FcαR is not inhibited by binding of IgA, such as endogenous IgA. Accordingly, a preferred binding agent binds to a site on an IgA receptor which is different from the binding site for IgA, such as endogenous IgA. Various methods can be used to determine the location of the binding site for IgA on the receptor. For example, monoclonal antibodies specific for different portions of the receptor can be prepared, e.g., by immunizing animals with recombinantly produced portions of the FcαR. These antibodies can then be used in competition binding experiments with IgA. Knowing the epitopes recognized by each of the monoclonal antibodies, it is possible to determine the site of binding of IgA. Alternatively, the IgA binding site can be determined by methods, such as X-ray crystallography. However, binding agents binding to a site on an IgA receptor which is different from the binding site for IgA can also be prepared without knowing where the IgA binding site is located. For example, it is possible to select antigen binding regions, the binding of which is not inhibited by IgA, by performing binding experiments and competition binding experiments in the presence of IgA. Accordingly, an antigen binding region of a binding agent, the binding of which is not inhibited by IgA, can be obtained by screening antigen binding regions for those whose binding to the IgA receptor is not inhibited by IgA by methods known in the art, e.g., ELISA or flow cytometry.

In a preferred embodiment, a binding region specific for an FcαR, the binding of which is not inhibited by IgA is derived from monoclonal antibody A77, an anti-FcαR antibody, the binding of which is not inhibited by IgA (Monteiro et al. (1992) *J. Immunol.* 148:1764). The antibody A77 has been produced by immunizing mice with acrylamide gel slices containing FcαR that was IgA affinity purified from human cell lysates. Monoclonal antibodies were screened according to three characteristics: staining of U937 cells at a higher density after PMA activation, selective reactivity with blood monocytes and granulocytes, and their ability to inmmunoprecipitate molecules of approximately 55 to 75 kDa from neutrophils and activated U937 cells. Other preferred binding agents contain at least one antigen binding region which is similar to the binding region of A77.

Monoclonal antibody A77 is capable of triggering Fc-receptor mediated effector cell activity. Accordingly, preferred binding agents include agents, the binding of which to the cell surface receptor is not blocked by IgA, which trigger Fc receptor mediated effector cell function. In one embodiment, the binding agent has an antigen binding region specific for an epitope that is recognized by monoclonal antibody A77. In another embodiment, the binding agent has an antigen binding region similar to an antigen binding region of A77. In yet another embodiment, the binding agent has an antigen binding region from A77.

Binding agents which are capable of binding to an FcαR, the binding of which is not blocked by IgA, and which are capable of triggering Fc-receptor mediated effector cell function can be selected using antibody A77 or an active portion thereof. For example, a population of agents or molecules binding FcαRs can be screened with monoclonal antibody A77 to obtain those having an epitope recognized by monoclonal antibody A77. FcαR binding experiments, competition binding experiments using IgA, and, activity tests, can then be used to confirm that the agents or molecules obtained in the screening have the desired characteristics.

A binding agent can bind with the same or a different affinity to FcαR as a type of IgA. A type of IgA is intended to include IgA1, IgA2, secretory IgA, serum IgA, monomeric IgA, dimeric IgA, or multimeric IgA. Thus, preferred binding agents of the invention bind to the FcαR with a higher affinity than a type of IgA. Determination of a binding affinity or avidity can be done according to methods known in the art.

A binding agent is intended to include an agent, e.g., a protein, peptide, or protein or peptide complex, which has the capacity to bind or to interact with a molecule, or a structure, such as a receptor on a cell surface. A binding agent can also bind to a soluble molecule. A binding agent can be a monospecific or a heterospecific binding agent. A heterospecific binding agent, used herein interchangeably with the term "multispecific binding agent" is intended to include bispecific, trispecific, tetraspecific, and other multispecific binding agents. A monospecific binding agent is intended to include binding agents having at least one antigen binding region binding essentially to a single molecule or antigen. A bispecific binding agent is intended to include binding agents having two different antigen binding regions, i.e., antigen binding regions which recognize different antigens or epitopes of an antigen. Such agents can have more than one antigen binding region of each type. A multispecific binding agent is intended to include agents having at least three different antigen binding regions. Multispecific binding agents can have more than one antigen binding region of each type. Preferred binding agents of the invention have at least one antigen-binding region for an Fc$\alpha$R.

In one embodiment of the invention, the binding agent comprises a monoclonal antibody, or binding fragment thereof, or derivatives therefrom. The term "monoclonal antibody" or "monoclonal antibody composition" as used herein refers to a preparation of antibody molecules of single molecular composition. A monoclonal antibody composition displays a single binding specificity and affinity for a particular epitope. In another embodiment of the invention, the binding agent comprises a chimeric antibody or binding fragment thereof or derives therefrom. A chimeric antibody is intended to include an antibody in which the variable regions are from one species of animal and the constant regions are from another species of animal. For example, a chimeric antibody can be an antibody having variable regions which derive from a mouse monoclonal antibody and constant regions which are human. In a preferred embodiment of the invention, the binding agent comprises a humanized antibody or binding fragment thereof or derives therefrom. The term humanized antibody is intended to include antibodies in which the hypervariable regions, also termed, the complementarity-determining regions (CDRS) are from one species of animal and the framework regions and constant regions of the antibody are from a different species animal species. In a humanized antibody of the invention, the CDRs are from a mouse monoclonal antibody and the other regions of the antibody are human. The term antibody as used herein is intended to include chimeric and humanized antibodies, binding fragments of antibodies or modified versions of such.

The term "antigen binding region of an antibody" is used interchangeably herein with the terms "antigen binding site of an antibody" and "binding determinant of an antibody" and is intended to include the region of an antibody that is involved in binding the antigen. The antigen binding site of an antibody comprises, but is not limited to, the amino acids of the antibody which contact the antigen. The antigen binding region can be the variable region of an antibody. The antigen binding region of an antibody can also be the hypervariable regions of an antibody. The antigen binding region of an antibody can also be the amino acid residues in the hypervariable region of an antibody which contact the antigen and/or which provide proper tertiary structure of the antigen binding region. Various methods are available for determining which amino acid residues of a variable region or hyper variable region of an antibody contact the antigen and/or are important in having a correctly folded antigen binding region. For example, mutagenesis analyses can be performed. In particular, it is possible to substitute one or more amino acids for other amino acids in a recombinantly produced antibody and to perform in vitro binding studies to determine the extent to which the binding affinity of the modified antibody for the antigen has changed compared to the non modified antibody. If binding has decreased due to substitution of an amino acid for another, the amino acid is most likely important in binding of the antibody to the antigen. Other methods for determining which amino acids of a variable region of an antibody are involved in binding of the antibody to an antigen are based on crystallographic analyses, e.g., X-ray crystallography.

The term "an antibody which binds specifically to an antigen" is intended to include an antibody which binds to the specific antigen with significantly higher affinity than binding to any other antigen, i.e., it is intended to define the specificity of an antibody as defined in the art. The terms "an antibody recognizing an antigen" and "an antibody specific for an antigen" are used interchangeably herein with the term "an antibody which binds specifically to an antigen".

Chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041–1043); Liu et al. (1987) *PNAS* 84:3439–3443; Liu et al., 1987, *J. Immunol.* 139:3521–3526; Sun et al. (1987) *PNAS* 84:214–218; Nishimura et al., 1987, *Canc. Res.* 47:999–1005; Wood et al. (1985) *Nature* 314:446–449; and Shaw et al., 1988, *J. Natl Cancer Inst.* 80:1553–1559.)

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, *Science* 229:1202–1207 and by Oi et al., 1986, *BioTechniques* 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution U.S. Pat. No. 5,225,539; Jones et al. 1986 *Nature* 321:552–525; Verhoeyan et al. 1988 *Science* 239:1534; and Beidler et al. 1988 *J. Immunol.* 141:4053–4060.

All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in International Application WO 94/10332 entitled, Humanized Antibodies to Fc Receptors for Immunoglobulin G on Human Mononuclear Phagocytes.

Human monoclonal antibodies (mAbs) directed against human proteins can be generated using transgenic mice carrying the complete human immune system rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856–859; Green, L. L. et al. 1994 *Nature Genet.* 7:13–21; Morrison, S. L. et al. 1994 *Proc. Natl. Acad. Sci. USA* 81:6851–6855; Bruggeman et al. 1993 *Year Immunol* 7:33–40; Tuaillon et al. 1993 *PNAS* 90:3720–3724; Bruggeman et al. 1991 *Eur J Immunol* 21:1323–1326).

Monoclonal antibodies can also be generated by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 *PNAS* 86:5728; Huse et al. 1989 *Science* 246:1275; and Orlandi et al. 1989 *PNAS* 86:3833). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al., 1991, *Biotechniques* 11:152–156). A similar strategy can also been used to amplify human heavy and light chain variable regions from human antibodies (Lanick et al., 1991, *Methods: Companion to Methods in Enzymology* 2:106–110).

In an illustrative embodiment, RNA is isolated from B lymphocytes, for example, peripheral blood cells, bone marrow, or spleen preparations, using standard protocols (e.g., U.S. Pat. No. 4,683,202; Orlandi, et al. *PNAS* (1989) 86:3833–3837; Sastry et al., *PNAS* (1989) 86:5728–5732; and Huse et al. (1989) *Science* 246:1275–1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combinantion, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27–9400–01; and the Stratagene SurZAP™ PTM phage display kit, catalog no. 240612), examples of methods and reagents particularly amenable for use in generating a variegated antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., *Nature* (1990) 348:552–554, complete $V_H$ and $V_L$ domains of an antibody, joined by a flexible $(Gly_4-Ser)_3$ linker can be used to produce a single chain antibody which can render the display package separable based on antigen affinity. Isolated scFV antibodies immunoreactive with the antigen can subsequently be formulated into a pharmaceutical preparation for use in the subject method.

Once displayed on the surface of a display package (e.g., filamentous phage), the antibody library is screened with the FcαR, or peptide fragment thereof, to identify and isolate packages that express an antibody having specificity for the FcαR. Nucleic acid encoding the selected antibody can be recovered from the display package (e.g., from the phage genome) and subcloned into other expression vectors by standard recombinant DNA techniques.

The term "binding fragment" of an antibody or protein capable of binding to an antigen is intended to include a fragment of the antibody or protein which is sufficient for binding to the antigen. Binding of a binding fragment of an antibody to an antigen can be with the same affinity or a different affinity, e.g., lower or higher affinity, as binding of the whole antibody to the antigen. Examples of binding fragments encompassed within the term antibody include: a Fab fragment consisting of the $V_L$, $V_H$, $C_L$ and $C_{H1}$ domains; an Fd fragment consisting of the $V_{H\ and\ CH1}$ domains; an Fv fragment consisting of the $V_L$ and $V_H$ domains of a single arm of an antibody; a dAb fragment (Ward et al., 1989 Nature 341:544–546) consisting of a $V_H$ domain; an isolated complementarity determining region (CDR); and an F(ab')$_2$ fragment, a bivalent fragment comprising two Fab' fragments linked by a disulfide bridge at the hinge region. These antibody fragments are obtained using conventional techniques well-known to those with skill in the art, and the fragments are screened for utility in the same manner as are intact antibodies.

The term binding fragment is also intended to include a binding fragment from a molecule which is not an antibody, for example a receptor or a ligand of a receptor. Accordingly, a binding fragment of a ligand of a receptor is a fragment of the ligand which is sufficient to bind to the receptor.

A binding fragment, e.g., a binding fragment of an antibody or of a ligand, can be an active or functional binding fragment. Accordingly, an active or functional binding fragment is intended to include binding fragments which are capable of triggering at least one activity or function triggered by the full length molecule. For example, an active binding fragment of monoclonal antibody My 43 or A77 is a fragment of the antibody that is capable of binding to the FcαR and triggering a receptor mediated effector cell activity, e.g., production of superoxide anion.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances. Antibodies in which amino acids have been added, deleted, or subsituted are referred to herein as modified antibodies or altered antibodies.

The term modified antibody is also intended to include antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody. Any modification is within the scope of the invention so long as the binding agent has at least one antigen binding region specific for an FcαR and triggers at least one effector function.

Specific binding agents with high affinities for a receptor can be made according to methods known to those in the art, e.g, methods involving screening of libraries (Ladner, R. C., et al., U.S. Pat. No. 5,233,409; Ladner, R.C., et al., U.S. Pat. No. 5,403,484). Further, the methods of these libraries can be used in screens to obtain binding determinants that are mimetics of the structural determinants of antibodies.

In particular, the Fv binding surface of a particular antibody molecule interacts with its target ligand according to principles of protein-protein interactions, hence sequence data for $V_H$ and $V_L$ (the latter of which may be of the κ or λ chain type) is the basis for protein engineering techniques known to those with skill in the art. Details of the protein surface that comprises the binding determinants can be obtained from antibody sequence information, by a modeling procedure using previously determined three-dimensional structures from other antibodies obtained from NMR studies or crytallographic data See for example Bajorath, J. and S. Sheriff, 1996, Proteins: Struct., Funct., and Genet. 24 (2), 152–157; Webster, D. M. and A. R. Rees, 1995, "Molecular modeling of antibody-combining sites," in S. Paul, Ed., Methods in Molecular Biol. 51, Antibody Engineering Protocols, Humana Press, Totowa, N.J., pp 17–49; and Johnson, G., Wu, T. T. and E. A. Kabat, 1995, "Seqhunt: A program to screen aligned nucleotide and amino acid sequences," in Methods in Molecular Biol. 51, op. cit., pp 1–15.

Binding agents of the invention include those comprising an antigen binding site that is derived from an antibody and which is grafted onto a molecule which is not an antibody. For example, an antigen binding region can be grafted onto a peptide or protein. In a particular embodiment, one portion of the antigen binding region, e.g., the portion similar to the antigen binding region from the light chain of an antibody, is grafted onto one protein or peptide and the other portion of the antigen binding region, e.g., the portion similar to the antigen binding region from the heavy chain of an antibody, is grafted onto another protein or peptide. In a preferred embodiment of the invention, the two proteins or peptides having each a portion of the antigen binding region are linked, e.g., by chemical linkage, recombinantly, or by non covalent interaction, such as to produce a protein having an antigen binding site specific for an FcαR for human IgA., which triggers at least one Fc receptor-mediated effector cell function.

An antigen binding region can also be obtained by screening various types of combinatorial libraries with a desired binding activity, and to identify the active species, by methods that have been described. For example, phage display techniques (Marks et al. (1992) J Biol Chem 267:16007–16010) can be used to identify proteins binding FcαRs. Phage display libraries have been described above.

In one embodiment, a variegated peptide library is expressed by a population of display packages to form a peptide display library. Ideally, the display package comprises a system that allows the sampling of very large variegated peptide display libraries, rapid sorting after each affinity separation round, and easy isolation of the peptide-encoding gene from purified display packages. Peptide display libraries can be in, e.g., prokaryotic organisms and viruses, which can be amplified quickly, are relatively easy to manipulate, and which allows the creation of large number of clones. Preferred display packages include, for example, vegetative bacterial cells, bacterial spores, and most preferably, bacterial viruses (especially DNA viruses). However, the present invention also contemplates the use of eukaryotic cells, including yeast and their spores, as potential display packages. Phage display libraries are described above.

Other techniques include affinity chromatography with an appropriate "receptor", e.g., FcαR, to isolate binding agents, followed by identification of the isolated binding agents or ligands by conventional techniques (e.g., mass spectrometry and NMR). Preferably, the soluble receptor is conjugated to a label (e.g., fluorophores, colorimetric enzymes, radioisotopes, or luminescent compounds) that can be detected to indicate ligand binding. Alternatively, immobilized compounds can be selectively released and allowed to diffuse through a membrane to interact with a receptor.

Combinatorial libraries of compounds can also be synthesized with "tags" to encode the identity of each member of the library (see, e.g., W.C. Still et al., International Application WO 94/08051). In general, this method features the use of inert but readily detectable tags, that are attached to the solid support or to the compounds. When an active compound is detected, the identity of the compound is determined by identification of the unique accompanying tag. This tagging method permits the synthesis of large libraries of compounds which can be identified at very low levels among to total set of all compounds in the library.

In a specific embodiment of the invention, the binding agent comprises an antigen binding region from a monoclonal antibody specific for anti-FcαR for human IgA. A monoclonal anti-Fc-alpha receptor antibody of this invention can be produced by a variety of techniques, including conventional monoclonal antibody methodology e.g., the standard somatic cell hybridization technique of Kohler and Milstein, *Nature* 256:495 (1975). Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are well known in the art. Fusion partners (e.g., murine myeloma cells) and fusion procedures are also well known.

Various antigens or forms of antigen can be used to immunize animals for the production of monoclonal antibodies to an FcαR,which are capable of triggering an Fc receptor mediated effector cell function. For example, human cells bearing Fc-alpha receptor, such as macrophages, monocytes, neutrophils, eosinophils, polymorphonuclear cells and other myeloid cells, can be used to immunize an animal for production of monoclonal antibody. Human cells for immunization include primary cells, i.e., cells obtained from a subject, or cell lines. For example, monocytic U937 cells or HL-60 cells can be used. It is preferable to treat the cells prior to injection with an agent, that will activate them and/or augment the expression of receptors for IgA. Such agents include, but are not limited to Phorbol Myristic Acetate (PMA) (Sigma Chemical Co., St. Louis, Mo.), interferon-λ (IFN-λ) (e.g., 300 IU/ml of IFN-λ for four days. Genentech, South San Fransisco, Calif.), or I-25 dihydroxy-vitamin D3 (Hoffmnan LaRoche, Nutley, N.J.). Treatment of cells with vitamin D3 can be done by incubating cells at 1 to 2×10$^6$ cells/ml for 7 days in the presence of 10$^{-7}$ M I-25 dihydroxy-vitamin D$_3$ Maximal FcαR cell surface expression on U937-like cells (U937-α cells) treated with PMA has been shown to occur after 24 hours of treatment. Furthermore, incubation of appropriate cells with IgA will also result in an increase of FcαR level on the cell surface.

It may also be preferable to measure the surface level of the FcαR, prior to immunization of an animal with the cells. This can be done, e.g., by determining the level of binding of hunan IgA, such as by ELISA or by flow cytometry. Thus, it may be beneficial to determine the amount of inducer and the length of induction that result in the highest level of the FcαR prior to using the cells for preparing the binding agent.

Employing the methodology described, a monoclonal antibody (mAb) My 43 of the IgM class which binds specifically to monocyte and polymorphonuclear (PMN) cell IgA receptors was developed, based on its ability to block IgA mediated rosettes and phagocytosis. This antibody recognizes a surface molecule which triggers function since monocytes and PMNs secrete superoxide when treated with this antibody.

Alternatively, the receptor for immunization of an animal can be prepared from lysates of human cells which express the receptor, e.g., a human monocytic cell. In another mode, a partially purified preparation of the receptor can be made by lysing receptor-bearing cells and then purifying the receptor by immunoadsorbant chromatography. Cells can be lysed in a buffer containing a detergent such as NP40. The immunoadsorbent can be prepared by attaching human IgA to a water-insoluble material such as an activated Sepharose™ resin. Human IgA can be prepared as follows. Human dimer IgA1 paraproteins (Sa IgA and Ca IgA) can be purified from myeloma sera by gel chromatography on Sepharose CL-6B (Pharnacia Fine Chemicals). The peak corresponding to dimer IgA can be cleared of contaminating IgG on protein A-Sepharose CL-6B; these preparations should contain less than 0.5 μg IgG/mg IgA by ELISA (Southern Biotechnology Associates, Birmingham, Ala.). The Sepharose resin with attached human IgA is poured into a column. The cell lysate is passed through the column under conditions which permit adsorption of the cellular Fc receptor protein by the IgA coupled to the resin. The adsorbed Fc receptor protein can be eluted with a mildly acidic elusion buffer. The purified receptor can then be used for immunization of an animal to produce anti-receptor monoclonal antibody. Such a method has been used succcessfully to produce monoclonal antibodies to human FcαR (Monteiro, et al. (1992) *J. Immunol.* 148: 1764). These monoclonal antibodies include A3, A59, A62, and A77.

Other antigens for immunizing animals for the production of monoclonal antibodies of the invention include recombinant forms of a receptor for IgA. Receptors for human IgA on monocyte/macrophages and neutrophils are glycosylated transmembrane proteins of 55 to 75 kDa that can bind both monomeric and polymeric forms of IgA1 and IgA2 antibodies. A cDNA encoding an FcαR has been cloned from a cDNA library for U937 cells (Maliszewsli, et al. (1990) *J. Exp. Med.* 172:1665). Receptors for human IgA can be produced recombinantly by, e.g., expressing a nucleic acid encoding such a receptor in a suitable host cell. Preferred host cells include bacteria and yeast. Even more preferred host cells are mammalian cells, since production of a receptor in a mammalian cell is likely to result in production of a glycosylated receptor. Techniques for production of a receptor for human IgA or of an extracellular portion thereof, by recombinant means are well known in the art and can be found in e.g., molecular biology protocol manuals.

Several assays can be performed to show that a binding agent of the invention specifically bind to an FcαR, such as human FcαR. For example, binding assays comparing binding of the binding agent and that of IgA to a variety of cells, some of which are bound by IgA (e.g., monocytes and macrophages) and some of which are not bound by IgA (e.g., K-562 cells), can be performed. The binding agent of the invention should bind substantially to the same set of cells as IgA. Competition binding experiments using the binding agent and IgA will indicate whether both agents recognize the same epitope. Binding experiments can be flow cytometry experiments, indirect imrnunofluorescence assays, or ELISAs among others. Further, IgA and the binding agent should immunoprecipitate a protein having similar molecular weight form the same cell. In addition, preclearing with IgA of a cell lysate having a FcαR should result in immunoprecipitation of less protein with the binding agent than in the absence of preclearing. Similarly, preclearing with the binding agent of the cell lysate should result in immunoprecipitation of less protein with IgA than in the absence of preclearing. Other tests for showing that the same antigen is recognized by a binding agent of the invention and IgA are known in the art. In addition, since FcαRs have been cloned, e.g., human FcαR, it is possible to use recombinantly produced FcαR or portions thereof or cells transfected to express FcαR to show binding of a binding agent to FcαR.

Preferred binding agents of the invention stimulate phagocytosis of target cells by effector cells when the binding agent links the target cell to the effector cell. For example, preferred bispecific binding agents of the invention have at least one antigen binding region specific for an FcαR and one antigen binding region to an epitope on a target cell can induce phagocytosis of the target cell. In fact, it has been shown that a heteroantibody of My 43 linked to antierythrocyte F(ab)'2 mediates erythrocyte phagocytosis by monocytes. Phagocytosis assays can be performed as follows. Packed target cells, e.g., ox erythrocytes (OE) (10 $\mu$l) are mixed for 16 hours at 10° C. with 20 $\mu$l of the F(ab')$_2$-Ig conjugates at concentrations previously determined to give maximal rosette formation. Heteroantibody-coated OE are washed, adjusted to $4\times10_7$ cells/ml, and are mixed with an equal volume of myeloid cells at $2\times10_6$ cells/ml. This mixture is incubated for 10 min at 37° C., and the cells are pelleted and incubated for a further 20 min, after which time noningested OE are lysed at 4° C. with buffered ammonium chloride. Phagocytosis can be assessed by microscopic examination of Wright's Giemsa (Sigma) stained cytospin preparations. At least 200 cells are counted in duplicate slides. Phagocytosis can be quantified as the percentage of cells containing one or more ingested erythrocyte(s).

A preferred binding agent triggers an oxidative burst, i.e., production of superoxide anion in an effector cell upon binding to an FcαR on the effector cell. For example, it was shown that My 43 triggeres production of superoxide anion by interferon-$\lambda$ treated U937 cells.

A superoxide assay can be performed on a solid phase or in solution. A solid phase superoxide assay can be performed as follows. Flat bottom 6-well PVC tissue culture places (Falcon Plastics Baxter Corporation, Bedford Mass.) can be treated for 30 minutes at room temperature with 1 ml per well of poly-L-lysine (Sigma, St. Louis, Mo.) at 100 $\mu$g/ml in PBS. After aspirating dry, glutaradehyde (2%, Sigma) can be added and incubated at room temperature for 15 min. After four washes with PBS, 1 ml of PBS containing the desired amount of Ig can be added, and incubated at ambient temperature for 2 hours. The wells can then be washed with PBS, filled with 100 mM glycine/0.1% BSA in PBS and incubated at 4° C. for 18 hours. They can then be washed twice with PBS and once in Krebs Ringer Hepes buffered salt solution (KRH) and 3×10+6 cells/well were added in KRH containing 1 mM KCN and 1 mg/mnl horse heart ferricytochrome c (Sigma). The cells can be spun down onto the plates for 5 minutes at 100×g and incubated at 37° C. PMA (Sigma) as added to positive controls to final concentrations indicated. After 30 min, the contents can be removed, spun down, and the supernatant read at 550 nm in a Dynatech spectrophotometer (Dynatech Labs, Chantilly, Va.).

Suspension superoxide assay can be performed as follows. Cells can be incubated with mAb at 4° C. for 45 minutes, then washed in KRH, resuspended in KRH containing 1 mM KCN and 1 mg/ml horse heart ferricytochrome c (Sigma), and incubation at 37° C. initiated. PMA (Sigma) can be added to positive controls at the concentrations indicated. After 30 minutes, the samples can be removed, spun down, and the supernatant read at 550 nm in a Dynatech spectrophotometer (Dynatech Labs).

The binding agents of the invention, e.g., antibodies can be used to target effector cells bearing Fc-alpha receptor. In a preferred embodiment of the invention, the binding agent comprises at least a first antigen binding region specific for FcαR and at least a second antigen binding region specific for a target epitope. For example, to target effector cells, bifunctional antibodies or hetero-antibodies can be employed. These antibodies have dual antigen binding specificity—one specificity for the Fc-alpha receptor, and one specificity for an epitope of the target cell. The Fc receptor, specificity mediates linkage to the effector cell through a known cytotoxic trigger molecule. The target cell specificity provides for recognition and binding to the target cell.

Bifunctional antibodies are single, divalent antibodies or antibody fragments or derivatives thereof which have at least two different antigen binding sites. Bifunctional antibodies for targeting have at least one binding site for an Fc receptor, and at least one binding site for a target cell epitope.

Heteroantibodies are two or more antibodies, antibody binding fragments (e.g., Fab), derivatives therefrom, or antigen binding regions linked together, at least two of which have a different specificity. In one embodiment, each antibody, fragment or antigen binding region of the heteroantibody have a different specificity. Preferred heteroantibodies for targeting comprise an antibody or antigen binding fragment specific for Fc receptor for IgA, coupled to an antibody or antigen binding fragment thereof specific for a target cell epitope.

The binding agents, e.g, multispecific molecules, can be prepared by a number of methods. For example, both specificities can be encoded in the same vector and expressed and assembled in the same host cell. This method is particularly useful where the multi-specific molecule is a mAb×mAb, mab×Fab, Fab×F(ab')$_2$ or ligand×Fab fusion protein. A binding agent, e.g., a bispecific molecule of the invention can be a single chain molecule, such as a single chain bispecific antibody, a single chain bispecific molecule comprising one single chain antibody and a binding determinant, or a single chain bispecific molecule comprising two binding determinants. Multispecific molecules can also be single chain molecules or may comprise at least two single chain molecules. Methods for preparing bi- and multivalent antibodies are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the single chain molecules to their specific targets can be confirmed by bispecific ELISA, familiar to those skilled in the art. Alternatively, each specificity of a multispecific molecule can be generated separately and the resulting proteins or peptides chemically conjugated to one another. For example, two humanized antibodies or antibody fragments can be conjugated via sulfhydryl bonding of the C-terminus hinge regions of the two heavy chains.

Bifunctional antibodies can be produced by chemical techniques (see e.g., D. M. Kranz et al. (1981) Proc. Natl. Acad. Sci. USA 78:5807), by "polydoma" techniques (See U.S. Pat. No. 4,474,893, to Reading) or by recombinant DNA techniques. Heteroantibodies can also be produced by chemical techniques or by recombinant DNA techniquess. For example, heteroantibodies can be prepared by conjugating Fc receptor antibody with antibody specific for an epitope of a target cell. A variety of coupling or crosslinking agents can be used to conjugate the antibodies. Examples are protein A, carboiimide, and N-succinimidyl-3-(2- pyridyldithio) propionate (SPDP). SPDP is the preferred agent; procedures for crosslinking antibodies with this agent are known in the art. See e.g., Karpovsky et al. (1984) *J. Exp. Med.* 160:1686; Liu M. A. et al. (1985) *Proc. Natl. Acad. Sci USA* 82:8648. Other cross-linking agents include N-succinimidyl-S-acetyl-thioacetate (SATA) (Pierce Chemical Co., Rockford, Ill.), sulfosuccinimidyl 4-(N-maleimidomethyl) cyclohexane-1-carboxylate (sulfo-SMCC) (Pierce Chemical Co., Rockford, Ill.), and ortho-phylenedimaleimide (o-PDM). Other methods include those described by Paulus (Behring Ins. Mitt. (1985) No. 78, 118–132); Brennan et al. (Science (1985) 229:81–83), and Glennie et al. (J. Immunol. (1987) 139:2367–2375).

Employing the SPDP agent, bi-specific antibodies of the monoclonal antibody My 43 and Fab anti-erythrocyte antibodies were prepared and shown to promote phagocytosis by monocytes (whereas bi-specific antibodies of anti-RBC x-anti-beta2 microglobulin did not). Target cells are cells whose elimination would be beneficial to the host. One important type of cell is a tumor cell. Effector cells can be targeted with binding agents, e.g, bi-functional or heteroantibody having specificity for Fc αR and specificity for a tumor-associated or tumor-specific antigen.

Antibodies with a desired tumor specificity for production of binding agents, e.g., bifunctional antibody or heteroantibody, can be produced or can be selected from available sources. Monoclonal antibodies against tumor-associated antigens can be made by the methods of Koprowski et al. (U.S. Pat. No. 4,172,124). Many suitable anti-cancer antibodies are presently available.

Specific anti-tumor antibodies would include, but not be limited to:

| Antibody | Specificity |
| --- | --- |
| AML-2-23, PM-81, PMN-6, PMN-19 | Myeloid Leukemia |
| SCCL-1, SCCL-175 | Small Cell Carcinoma of the Lung |
| OC1-25, OVCT-3 | Ovarian Carcinoma |
| CDL-1, CDL-2, CDL-3, . . . CDL-13 | Colon Carcinoma |

Other tumor cells that can be targeted are tumor cells of any type of cancer, including cancer of breast, ovarian, prostate, testicular, lung, colon, rectum, pancreas, liver, central nervous system, kidney, head, neck, bone, blood, and lymphatic system. Preferred target antigens include carcinoembryonic antigen (CEA), gastrin releasing peptide receptor antigen, mucine antigens, EGF-R, HER2/neu, HER3, HER4, and TAG 72. TAG 72 is found, e.g., on tumors of the breast, colon, and ovary. An antigen binding region specific for CEA can be, e.g., from the single chain antibody, termed MFE-23, is described in Casey et al. (1994) *J. Immunol. Methods* 179:105 and Chester et al. (1994) *Lancet* 343:455. An anti-HER2/neu antibody is produced by the cell line 520C9 (Ring et al. 1991 J. Immunol. 28:915–917). Antibody H425 is a humanized version of anti-EGF-R antibody M425. An antibody for TAG 72 is monoclonal antibody cc49 described in published PCT application WO 93/11161, published PCT application WO 90/04410, corresponding to granted EP Patent No. 365 997; published PCT application WO 93/12231; and published PCT application WO 89/01783.

Yet other antigens can be antigens associated with B cell lymphomas, e.g, HLA-DR, CD74, CD79, CD20, CD37, and CD19. Antigens associated with other blood diseases are also within the scope of the invention. Accordingly, the invention also provides methods for treating blood cell disorders, such as leukemias and lymphomas.

Breast and ovarian cancers can be sex hormone dependent cancers. Breast tumors may be characterized by abnormally expressed receptors, e.g. those of the human-EGF-like receptor family (HER), for example HER-2, -3, and 4. The invention is not limited to these embodiments of HER antigens. The natural HER ligand, Heregulin, can be incorporated into a binding agent, e.g., bispecific antibody (BsAb) or multispecific molecule, as a means to target a breast tumor cell expressing one or more HER receptor during cancer. Further, heregulin molecules are binding determinants for heterodimeric HER receptors containing, eg. a monomer of each of HER-2, -3 or 4 in combination. In one embodiment, a binding agent comprises amino acids 171–239 of the heregulin β2 shown in U.S. Pat. No. 5,367,060. Other portions of heregulin β2, as well as portions of other heregulin molecules, such as those disclosed in U.S. Pat. No. 5,367,060 can also be used.

Binding agents of the invention can also be used for treating tumors of the central nervous systems. The nestin protein, which is expressed during normal mammalian fetal development, is expressed on tumors of the central nervous system, including most forms of brain cancer (McKay, D. G. Ronald, U.S. Pat. No. 5,338,839, Aug. 16, 1994). Nestin is also expressed on melanomas on the skin and on melanomas that have metastasized (V. A. Florenes, R. Holm, O. Myklebost, U. Lendahl, O. Fodstad, *Cancer Res.* 54:354–6, 1994), to other organs and are difficult to detect and treat. The preferred site of delivery for treatment of a brain tumor with the molecules of this invention is directly into the central nervous system or directly, to the brain via spinal injection or fine needle delivery. For a metastatic cancer, a preferred delivery route would be by direct injection into the circulation, or by the ex vivo blood methods described herein.

Other tumor types for which the methods of this invention are exemplified by, but are not limited to, Wilm's tumor (A. J. Buckler, K. M. Call, T. M. Glaser, D. A. Haber, D. E. Housman, C. Y. Ito, J. Pelletier, Rose, E. A. Rose, U.S. Pat. No. 5,350,840) a pediatric kidney cancer due to occurrence of a somatic mutation in the patient's single copy of a gene normally found in two intact copies. Wilm's tumor can be cured surgically in 95% of cases, and a binding agent is envisioned to be suitable as an adjunct therapeutic modality for surgical patients. Other examples of known cancer-associated proteins for which the compositions of matter and methods of the current invention are suitable include those associated with gastrointestinal cancer (R. Fishel et al., International Application WO 95/14085, May 26, 1995), those characterized by development of multiple drug resistance during chemotherapy (J. M. Croop et al., U.S. Pat. No. 5,198,344), and a large number of oncogenes well known to the skilled artisan such as Rb, ras, and c-myc, the sequences of which are available for analysis to those with skill in the art. The compositions of this invention are, for example, suitable for inhibition of secreted enzymes such as matrix metalloproteinases, which are considered to potentiate tumor metastasis (Liotta, L. A., et al., (1991), Cell, 64:327–336). In the latter embodiment, a binding agent with a binding determinant to the matrix metalloproteinase and another for FcαR would facilitate inhibition and clearance of these enzymes from in situ activity. If used in conjunction with standard surgical and chemotherapeutic regimens, the compositions are foreseen to reduce cancer re-occurrence and enhance long-term survival.

In addition to tumor cells, the effector cell can be targeted against auto-antibody producing lymphocytes for treatment of autoimmune disease or an IgE-producing lymphocyte for treatment of allergy. Autoimmune disorders which can be treated with a binding agent of the invention include diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis. Thus, an autoimmune disease can be treated by, e.g., administering to a subject having an autoimmune disease a binding agent having at least one antigen binding region specific for a human Fcα R, and an antigen binding region specific for an epitope on an autoirnmune cell. In one embodiment the target epitope is an epitope on an autoantibody. Accordingly, resting B lymphocytes having autoantibodies on their surface can be targeted and destroyed by a multispecific antibody bridging the B lymphocyte and an effector cell having an FcαR, thereby inducing an effector cell function, resuling in lysis of the B lymphocyte.

Similarly, binding agents having at least one binding specificity for an FcαR and at least one binding specificity for an epitope on a lymphocyte producing IgE can be used to treat allergies. The binding agent for use in treating allergy in a subject can also be a binding agent having at least one antigen binding region specific for an epitope on an IgE antibody. Accordingly, such a binding agent can link an effector cell having an FcαR and a target cell whose surface is coated with IgE, such as a basophil and a mast cell, resulting in lysis of the target cells. Such a treatment can also prevent binding of an antigen to the IgE molecules and thus prevent secretion by these cells of mediators involved in allergy, e.g., histamine. Additionally, the binding agent can bind soluble IgE and thereby prevent binding of IgE to mast cells and basophils. Allergies that can be treated by administering multispecific binding agents of the invention are described below.

The target can also be microorganism (bacterium or virus) or a soluble antigen (such as rheumatoid factor, or other auto-antibodies and toxins). A microorganism is intended to include pathogens, e.g., viruses, bacteria, fungi, protozoa. A microorganism can also be targeted by targeting a cell infected by a microorganism, such as a pathogen infected cell.

Accordingly, the invention provides methods for treating infectious diseases, by, e.g., administrering to a subject having an infectious disease an efficient amount of a binding agent having at least one antigen binding region specific for an FcαR and at least one antigen binding region specific for an epitope on a microorganism. The term "infectious disease" is meant to include disorders caused by one or more species of bacteria, viruses, fungi, and protozoans, which are disease-producing organisms collectively referred to as "pathogens." In this invention, pathogens are exemplified, but not limited to, *Mycobacterium tuberculosis, M. leprae, Pseudomonas aeruginosa, Shigella dysenteria, Salmonella typhi, S. paratyphi, Staphylococcus aureus, Streptococcus hemolyticus, Hemophilus pneumoniae, Escherichia coli* serotype 0157, Chlamydia species, Helicobacter species; HIV-1, -2, and -3, HTLV, FELV, HSV-I and -II, hepatitis B virus, (e.g., HBV major surface antigen), non-A non-B non-C hepatitis virus, Epstein Barr virus (EBV glycoprotein), pox viruses, rabies viruses; Aspergillus species; *Entamoeba histolytica*, Giardia species; Newcastle disease virus; *Toxoplasma gondii*; and *Candida albicans*. Obtaining unique epitopes from these organisms by screening proteins and by assaying peptides in vitro are commonly known to those skilled in the art. Thus, preferred binding agents of the invention have at least one antigen binding region specific for an epitope on any of these microorganisms.

In a preferred embodiment, the binding agent has an antigen binding region specific for an envelope glycoprotein of an HIV virus, e.g., gp41 of HIV. Also within the scope of the invention are binding agents specific for gp120 or CD4. In one embodiment, the binding agent derives from the human anti-HIV-1 IgG1 mAb, DZ33.

IgA plays an important role in mucosal defense and FcαRs have been found on effector cells, e.g., monocytes and macrophages, from mucosal areas (See e.g., Shen, L. and Collins, J. (1989) Immunology 68:491). For example, monocytes and macrophages at mucosal surfaces, e.g., the lung, were found to express FcαR (Shen, L. and Collins, J. (1989) Immunology 68:491). Accordingly, the invention provides methods for eliminating microorganisms or any unwanted cells from mucosal areas. Such methods are particularly useful in view of the fact that mucosal sites are often entry points for invading organisms and further in view of the fact that superoxide is a potent microbial agent. For example, oxygen metabolites, such as superanion have been shown to have bactericidal and bacteriostatic effects.

An antigen binding region to a target epitope can also be a ligand to a receptor, e.g, growth factors or differentiation factors, which can target the binding agent to cells having a receptor for these growth or differentiation factors. For example, a binding agent can comprise an epidermal growth factor (EGF), or at least a portion or modified form thereof that is capable of interacting with an epidermal growth factor receptor (EGF-R). The binding agent can also comprise a binding portion of heregulin. In another preferred embodiment of the invention, the ligand is a small peptide, such as bombesin, gastrin-releasing peptide (GRP), litorin, neuromedin B, or neuromedin C. The sequences of the peptides can be found, e.g., in U.S. Pat. No. 5,217,955, the content of which is incorporated herein by reference. The ligand can also be a modified form of any of these peptides. The modification can increase binding to the receptor, decrease binding, or not affect the binding to a receptor. The modification of the ligand can also transform an agonist into an antagonist, such that the ligand inhibits rather than stimulates cell proliferation. Modification of the ligand can be an addition, a deletion, a substitution, or a modification of at least one amino acid.

Effector cells for targeting can be human leukocytes, preferably macrophages. Other cells include monocytes and other IgA-receptor bearing cells. If desired, effector cells for targeting can be obtained from the host to be treated.

The targeted effector cells, i.e., effector cells coated with binding agent of the invention, can be administered as a suspension of cells in a physiologically acceptable solution. The number of cells administered can be in the order of $10^8$–$10^9$ but will vary depending on the therapeutic purpose. In general, the amount will be sufficient to obtain localization at the target cell and to effect target cell killing by antibody dependent-mediated cytolysis (ADCC). Routes of administration can also vary. In tumor therapy, for instance, depending upon the localization of a tumor, the targeted effector cells could be administered intravenously, or directly into tumor sites; as for example, directly into the peritoneal cavity in the case of ovarian carcinoma.

Therapy with targeted effector cells can be performed in conjunction with other techniques for removal of targeted cells. For example, anti-tumor therapy with binding agents, e.g., bifunctional antibodies and/or effector cells armed with binding agents, e.g., bifunctional (hetero)antibody can be used in conjunction with surgery, chemotherapy or radiotherapy. Additionally, combination immunotherapy may be used to direct two distinct cytotoxic effector populations toward tumor cell rejection. For example, anti-tumor antibodies linked to anti-Fc-gammaRI or anti-T3 (will trigger cytolytic T lymphocytes to lyse tumor cells) may be used in conjunction with IgA-receptor specific binding agents, e.g., heteroantibodies. Protocols based on these concepts may be especially effective in removing residual tumor cells in patients induced into remission by chemotherapy and irradiation.

The monospecific or multispecific binding agent of the invention, which binds an FcαR, and which comprises, e.g., an anti-Fc-alpha receptor antibody or binding fragment thereof of this invention has additional utility in therapy and diagnosis. The binding agent, e.g., Fc receptor antibody, itself can be a targeting binding agent or antibody (i.e., to target for cells bearing an Fc-alpha receptor). For example, the binding agent, e.g, antibody can be used to target lipid vesicles containing anticancer drugs for treatment of certain hematological cancers (e.g. acute myeloid leukemia), or to target lipid vesicles containing factors (such as gamma-IFN) which activate monocytes. The antibody, if of the appropriate murine IgG subclass (e.g., IgG2a), can be used directly in vivo to eliminate Fc-alpha-receptor-bearing cells (e.g., myeloid leukemia cells) via natural complement or ADCC mechanisms.

In another embodiment, a molecule, e.g., an antigen, is linked either recombinantly or chemically to a monospecific or multispecific binding agent of the invention. Such a binding complex can be used, e.g., to induce a specific immune response against a chronic infection, against a tumor or cancer cell, or to deplete antigen in the circulation. In yet another embodiment, the antigen is attached to the binding agent of the invention through an antigen binding region specific for the said antigen. Accordingly, within the scope of the invention are molecular or binding complexes comprising an antigen and a binding agent having at least one antigen binding region to an FcR and at least one antigen binding region to which the antigen binds. The antigen can be linked non covalently or covalently, such as by using chemical cross linking agents, to the binding agent.

The term "antigen" means any natural or synthetic immunogenic substance, a fragment or portion of an immunogenic substance, a peptidic epitope, or a hapten. In one embodiment of the invention, a binding agent is employed to target an antigen, e.g., tetanus toxoid to the cell to enhance the processes of internalization and presentation by these cells, and ultimately, to stimulate an immune response therein.

One type of antigen can be an allergen. An "allergen" refers to a substance that can induce an allergic or asthmatic response in a susceptible subject. The number of allergens that elicit a sensitive response in a proportion of a population is enormous, and includes pollens, insect venoms, animal dander, dust mite proteins, fungal spores and drugs (e.g. penicillin). Examples of natural animal and plant allergens include proteins specific to the following genera: Felis (*Felis domesticus*); Canis (*Canis familiaris*); Dermatophagoides (e.g. *Dermatophagoides farinae*); Periplaneta (e.g. *Periplaneta americana*); Ambrosia (*Ambrosia artemiisfolia*; Lolium (e.g. *Lolium perenne* or *Lolium multiflorum*); Cryptomeria (*Cryptomeria japonica*) ; Alternaria (*Alternaria alternata*); Alder; Alnus (*Alnus gultinosa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*) Thuya (e.g. *Thuya orientalis*); Chamaecyparis (e.g. *Chamaecyparis obtusa*); Agropyron (e.g. *Agropyron repens*); Secale (e.g. *Secale cereale*); Triticum (e.g. *Triticum aestivum*); Dactylis (e.g. *Dactylis glomerata*); Festuca (e.g *Festuca elatior*); Poa (e.g. *Poa pratensis* or *Poa compressa*); Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*).

Many allergens are found in airborne pollens of ragweed, grasses, or trees, or in fungi, animals, house dust, or foods. As a class, they are relatively resistant to proteolytic digestion. Preferable allergens are those which bind to IgE on mast cells and basophils, thereby causing a range of symptoms from inflammation and asthma to a type I anaphylaxis hypersensitivity reaction.

In another preferred embodiment, a binding determinant is specific for an antigen on an infectious disease agent or an infected cell, as defined supra. In some cases, it may be desirable to couple a substance which is weakly antigenic or nonantigenic in its own right (such as a hapten) to a carrier molecule, such as a large immunogenic protein (e.g., a bacterial toxin) for administration. In these instances, the binding reagent can be made to bind an epitope of the carrier to which the substance is coupled, rather than an epitope of the substance itself.

The antigen that can be linked either directly, or indirectly, to a binding agent of the invention can be soluble or particulate; it may carry B cell epitopes, T cell epitopes or both. The antigen can be bacterial, fungal, viral or parasitic in origin. Often, the antigen will comprise a component of the surface structure of a pathogenic organism, or a surface structure in a cell infected by a pathogenic organism. For example, the antigen can comprise a viral surface structure such as an envelope glycoprotein of human immunodeficiency virus (HIV) or the surface antigen of hepatitis virus. In addition, the antigen can be associated with a diseased cell, such as a tumor cell, against which an immune response may be raised for treatment of the disease. The antigen can comprise a tumor-specific or tumor-associated antigen, such as the HER-2/neu proto-oncogene product which is expressed on human breast and ovarian cancer cells (Slamon et al. (1989) *Science* 244:707). Another important cancer antigen which comprises a target of the BsAb of this invention is TAG 72, which has been identified on about 90% of colorectal cancers, 85% of breast tumors, and 95% of ovarian tumors (Johnson et al.(1986) *Cancer Res.* 46:850–897; Bodmer, M. et al., European Patent Specification 0 348 442 B1; Mezes, P. et al. International Application WO 93/12231).

In another embodiment of the invention, a binding agent is linked to an antigen that has been modified, such that its effect on T cell activation is modified upon presentation of the modified antigen to the T cell by an antigen presenting cell. Allan et al. have in fact shown that substitution of one or more amino acids of a peptide that stimulates T cells, e.g., stimulates T cell proliferation, can result in an antigen which fails to stimulate the T cell or which induces anergy in the T cell. Such modified peptides are termed Altered Peptide Ligands (APL). Accordingly, such APLs can be linked to binding agents of the invention, e.g., bispecific or multispecific molecules having at least one binding specificity for the Fcγ RI. Upon phagocytosis of these molecules by antigen presenting cells and presentation to T cells, the proliferation of the T cells may be inhibited or anergized. Accordingly, administration to a subject of a binding agent comprising (a) at least one altered peptide of an antigen which normally stimulates T cells, but which upon modification induces anergy of the T cells, and (b) at least one antigen binding region specific for an FcαR can result in induction of tolerance of the subject to the antigen. Thus, such binding agents of the invention can be used to tolerize a subject to a variety of antigens, e.g., auto-antigens. Thus, depending on the antigen used, the methods of the invention provide methods for increasing an immune response, i.e., by using an antigen which stimulates T cells, and the invention also provides methods for reducing an immune response, either by inhibiting T cell stimulation or by inducing anergy of the T cells.

Binding agents of the invention can also be used to target cells expressing FcαR, for example for labeling such cells. For such use, the binding agent can be linked to a molecule that can be detected. Thus, the invention provides methods for localizing ex vivo or in vitro cells having an FcαR.

Binding agents of the invention can also be used to modulate FcαR levels on effector cells, such as by capping and elimination of receptors on the cell surface. Mixtures of anti-Fc receptors can also be used for this purpose.

Binding agents of the invention which have complement binding sites, such as portions from IgG 1, 2, or 3 or IgM which bind complement can also be used in the presence of complement. Accordingly, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. Alternatively, such binding agent coated target cell can also be lysed by complement.

Binding agents to be used in vitro can also be administered together with complement. Accordingly, within the scope of the invention are compositions comprising binding agents and serum or complement. It may be advantageous to administer such a composition, since the complement will be located in close proximity to the binding agent. Alternatively, the binding agent and the complement or serum can be administered separately.

The invention further provides nucleic acid molecules encoding binding agents which have at least one antigen binding region binding to an FcαR. Also included are nucleic acid molecules encoding portions of a binding agent, such as a single antigen binding region. Expression vectors for expressing a nucleic acid encoding a binding agent or portion thereof in a host cell, e.g., procaryotic cell including bacterial cell, or a eukaryotic cell including a yeast cell or a mammalian cell.

Also within the scope of the invention are cells, e.g., host cells, producing a binding agent or a portion thereof. A cell can be a cell producing a recombinant binding agent or portion thereof. For example, the cell can be a cell producing a single chain binding agent having one or two antigen binding regions. Alternatively, the cell can be a hybridoma producing a monoclonal antibody having at least one binding region specific for an FcαR A cell can also be a trioma or a quadroma, which can produce bispecific monoclonal antibodies.

Further within the scope of the invention are methods for treating a disorder, such as an autoimmune disorder, a cancer, or a pathogenic infection with a combination of binding agents. A combination of binding agents can be a combination of a first binding agent having at least one antigen binding region specific for an FcαR and at least one antigen binding region to a target antigen and a second binding agent having an antigen binding region to a different epitope of the same target antigen and/or receptor. A preferred combination of binding agents include a binding agent having at least one antigen binding region specific for an FcαR and a binding agent having at least one antigen binding region specific for a receptor for IgG, such as the high affinity receptor for IgG. Alternatively, the second binding agent can be a binding agent having at least one antigen binding region specific for an IgE receptor, i.e., Fcϵ receptor, an Fcδ receptor and/or an Fcμ receptor. Such binding agents are further described in U.S. Pat. No. 4,954,617, European Patent EP 255 249 B1, in published international applications PCT/US87/01648, PCT/US95/02750, PCT/US91/07283, PCT/US90/03751, PCT/US93/09556, and PCT/US90/06030, which are expressly incorporated by reference herein. A preferred anti-FcγR antibody is humanized mAb 22 antibody. The humanized mab 22 antibody producing cell line was deposited at the American Type Culture Collection on Nov. 4, 1992 under the designation HA022CL 1 and has the accession no. CRL 11177.

An even more preferred embodiment of the method for eliminating unwanted cells or antigens in a subject involves treating the subject in addition with an agent that enhances the number or activity of Fcαreceptors, for example, treating the subject with a cytokine. Preferred cytokines, lymphokines or growth factors for administration during treatment with the invented composition treatment include at least one of G-CSF, GM-CSF, IFN-γ, TNF, and interleukins such as IL-2, IL-10 and IL-12. Protocols involving treatment with the molecules of the subject invention and more than one additional therapeutic agent are envisioned. Another preferred embodiment of the invention is a method for eliminating an unwanted cell in a subject, comprising obtaining an aliquot of a sample of blood or blood cells from said subject, treating said blood or blood cells ex vivo with a therapeutically effective dose of a multispecific binding molecule of the invention in a pharmaceutically acceptable carrier, said binding molecule comprising a first binding determinant which binds an Fcα receptor and a second binding determinant which binds one or more target antigens, and returning said treated blood or blood cells to the subject. Preferably, the cells of the sample of blood are isolated and expanded in culture, and more preferably, the cells of said sample of blood are treated with agents that enhance the number or activity of Fcα receptors.

In yet another embodiment, the invention provides a method for immunizing a subject against a cancer antigen or an antigen found on a pathogen or a cell infected by a pathogen, comprising administration in a pharmaceutically acceptable carrier of a composition of a binding agent bearing one or more antigens of a pathogenic infectious organism, or of an antigen of infected cells, or of a cancer cell. Accordingly, the binding agents can be used as vaccines or can be added to vaccine formulations.

Also within the scope of the invention are kits comprising a binding agent having at least one antigen binding region specific for anFcαR, and instructions for use. The kit can further contain a least one additional reagent, such as complement, or a second binding agent.

The binding agent can be used in vivo or in vitro. For in vivo use, the binding agents of the invention can be incorporated into pharmaceutical compositions suitable for administration to a subject in vivo. In a preferred embodiment, the pharmaceutical composition comprises binding agent compound, or molecular complex of the invention and a pharmaceutically acceptable carrier. In yet another embodiment of the present invention, the pharmaceutical composition can be administered by combination therapy, i.e., combined with other agents. For example, the combination therapy can include a composition of the present invention with at least one anti-cancer agent, one antibiotic, one vaccine, or other conventional therapy. Exemplary anti-cancer agents include cis-platin, adriamycin, and taxol. Exemplary antibiotics include isoniazid, rifamycin, and tetracycline. Other agents which can be administered together with a binding agent of the invention, for example, for treating AIDS, include AZT, DDI, cefachlor, nystatin, and acyclovir As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., binding agent, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1–19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) *J. Neuroimmunol.* 7:27). Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred per cent, this amount will range from about 0.01 per cent to about ninety-nine percent of active ingredient, preferably from about 0.1 per cent to about 70 per cent, most preferably from about 1 per cent to about 30 per cent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

In certain embodiments, the compounds of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al (1995) *Am. J. Physiol.* 1233:134), different species of which may comprise the formulations of the inventions, as well as components of the invented molecules; p 120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

A "therapeutically effective dosage" preferably inhibits tumor growth or pathogen infection by at least about 20%, more preferably by at least about 40%, even more preferably by at least about 60%, and still more preferably by at least about 80% relative to untreated subjects. The ability of a compound to inhibit cancer or infectious disease can be evaluated in an animal model system predictive of efficacy in human tumors and infectious diseases. Alternatively, this property of a composition can be evaluated by examining the ability of the compound to inhibit, such inhibition in vitro by assays well-known to the skilled practitioner. A therapeutically effective amount of a therapeutic compound can decrease tumor size, prevent or delay death of infected tissues or organs, decrease fever and white cell count, improve CD4 count or otherwise ameliorate symptoms in a subject. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as manitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier. As used herein "pharmaceutically acceptable carrier" includes any and all solvents, dispersion media, liposome formulations and coatings, antibacterial and antifungal agents, isotonic and absorption delaying agents, and other discussed above. The use of such media and agents for formulation of pharmaceutically active substances that are stable to oral administration is well known in the art. Except insofar as any conventional media or agent is incompatible with the active compound, use thereof in the therapeutic compositions is contemplated. Supplementary active compounds can also be incorporated into the compositions.

This invention is further illustrated by the following examples which should not be construed as limiting. The contents of all references and published patent applications cited throughout this application are hereby incorporated by reference. The following methodology described in the Materials and Methods section was used throughout the examples set forth below.

EXAMPLE 1

Preparation of monoclonal anti-FcαR antibody My 43

This Example describes how the My 43 monoclonal antibody was obtained.

BALB/c mice were immunized with $1 \times 10^7$ monocytes at 10-day intervals. The monocytes were prepared as follows. Mononuclear cells enriched for monocytes were obtained by cytopheresis of peripheral blood from normal volunteers. These cells, which contained >50% monocytes, were further purified by centrifugation over Ficoll Hypaque (Pharmacia Fine Chemicals, Piscataway, N.J.). The mononuclear cell layer was washed five times in RPMI 1640 medium and resuspended in 10% FCS at $5 \times 10^7$ cells/ml in a 50 ml polypropylene tube. The tube was rotated for 90 min at 4° C., causing the monocytes to clump, and was then placed upright in an ice bath for 30 minutes, allowing the clumped cells to settle as a pellet. Sedimented cells were then washed three times in RPMI 1640 medium, and contained greater than 90% monocytes, the remainder being lymphocytes (Shen et al. (1986) *Clin. Exp. Immunol.* 65:387).

Five days after the second immunization with monocytes, the mice were killed and spleen cells hybridized with NS-1 nonsecreting myeloma cells as previously described (Ball et al. (1982) *J. Immunol.* 128:1476). Resulting hybridomas were tested for production of antimonocyte mAb by indirect immunofluorescence. Antimonocyte mAbs were tested for blocking of FITC-IgA binding to monocytes as follows. Cells were incubated with medium or hybridoma supernatants for 45 minutes at 4° C., washed, and mixed with 25 μl FITC-labeled human IgA1 (Sa) at 100 μg/ml or FITC-labeled human IgG1 at 40 μg/ml. To determine specificity of binding, unlabeled IgA or IgG (25 μl) was added to some aliquots to a final concentration of 5 mg/ml. After 1½hours at 4° C., the cells were washed once with PBS/0.1% BSA/ 0.05% $NaN_3$ (PBA) and fixed with 2% paraformaldehyde.

One hybridoma producing a mAb that blocked FITC-labeled IgA binding to human monocytes, My 43, was subcloned twice by limiting dilution. My 43 was determined to be of the IgM isotype by ELISA (Southern Biotechnology Associates). Ascites were produced by injecting $5 \times 10^6$ cells i.p. into pristane primed by BALB/c mice. IgM was purified from ascites by HPLC gel filtration by using a TSK 400 column (Bio-Rad) followed by passage through protein A-Sepharose 4b (Pharmacia).

EXAMPLE 2
Characterization of My 43

Further analyses with My 43 showed that mouse IgM did not inhibit binding of Ig in a general way. To evaluate the possibility that My 43 nonspecifically inhibited binding of IgA to the monocyte surface due to steric effects, monocytes were treated with My 43 or other hybridoma supernatants with reactivity to monocytes, and then tested for their ability to bind FITC-labeled human Sa IgA or FITC-human IgG1. The amount of mAb bound to monocytes form the same preparation was assessed by indirect immunofluorescence and showed that My 43 blocked binding of IgA but not IgG1 and did so even though relatively low amounts of this antibody bound to monocytes as evaluated by the number of FITC anti-mouse Ig molecules bound. In contrast, other mAb which bound to monocytes at a much higher density did not interfere with IgA binding. Human IgG1 binding was not blocked by My 43, but was partially blocked by IV.3, which recognizes the human low affinity receptor for IgG (FcγRII), and by W6-32, an anti-HLA IgG2a anti-body whose Fc region binds the high-affinity Fc receptor for IgG (FcγRI).

It has previously been shown that HL-60 cells developed IgA Fc receptors after culture with $D_3$. HL-60 cells cultured for 7 days with calcitriol acquired ability to bind FITC-labeled IgA and also stained with My 43 more highly than untreated cells. Moreover, binding of FITC-IGA to these cells was inhibited by My 43. Peripheral lymphocytes, B-lymphocyte cell lines, and K-562 cells did not bind FITC-IgA or My 43.

Another measure of IgA receptor expression that has been widely used is the formation of rosettes with IgA-coated erythrocytes (E). The binding of IgA to IgA receptors is stabilized in this system by polymerization of IgA on the E surface. Although this complexed form of IgA probably binds with a greater avidity than soluble IgA, My 43 almost completely inhibited IgA rosettes, whereas PM-81 and IV.3, which bind to monocytes to an equal or greater extent than My 43, were not inhibitory. Consistent with the studies on FITC-labeled Ig binding, binding of IgG complexed on E was unaffected by My 43. Furthermore, rosette formation mediated by two different human IgA myeloma proteins was inhibited by My 43.

In other studies it was found that the phagocytosis of IgA-coated E was blocked by prior coating of monocytes with My 43, but not by other mAb which bound to the monocyte surface at a density equal or greater than My 43. By contrast, IgG-mediated phagocytosis was not inhibited. Similarly, $D_3$-treated HL-60 cells, which were able to ingest IgA-coated E, were unable to perform IgA-mediated phagocytosis after My 43 treatment, whereas their ability to ingest IgG-coated red cells was unaffected. On the other hand, IgG-mediated phagocytosis by monocytes and HL-60 cells was partially inhibited by the anti-FcγRII mAb IV.3.

The ability of My 43 to promote phagocytosis was tested by coating E with heteroantibodies composed of My 43 linked to F(ab')$_2$ fragments of rabbit anti-E antibodies. Heteroantibody composed of Fab BBM1 linked to F(ab')$_2$ anti-E antibodies served as a control. All preparations were used at concentrations giving maximal rosette formation. While BBM1 promoted far greater rosette formation than My 43, phagocytosis was induced by My 43 heteroantibody-coated red cells and not BBM1-coated red cells.

The heteroantibodies were prepared as follows. Conjugates of IgA, IgG, or purified mAb linked to Fab anti-ox erythrocytes (anti-OE) were made by using the bifunctional reagent SPDP (Pharmacia, Uppsala, Sweden). F(ab')$_2$ anti-OE was prepared from rabbit anti-OE IgG (Cooper Biomedical Malvern, PA) by pepsin cleavage and passage through protein A CL-6B. IgA, or IgG and F(ab')$_2$ anti-OE (at 1 to 3 mg/ml) were treated separately with an eightfold molar excess of SPDP for 2 hours at 18° C. SPDP-treated anti-OE Fab was dialyzed in PBS, pH 7.2, SPDP-treated IgA, IgG, or mAb were dialyzed in 0.1 M acetate, 0.1 M NaCl, pH 4.5, treated with 0.02 M dithiothreitol (30 min) and passed through a G.25 sephadex column (Pharmacia), equilibrated in 0.1 M phosphate, 0.1 M NaCl, pH 7.5. Equimolar amounts of the anti-OE F(ab')$_2$ and IgA or IgG were then mixed and incubated at 18° C. for 4 hours, after which cross-linking was terminated with 2mM iodacetamide. Preparations contained less than 15% non-cross-linked Ig. The monocytes were prepared as described above.

The results indicate that phagocytosis was induced by My 43 x(Fab)'2 anti-OE heteroantibody coated cells and not by anti-β32 microglobulinx(Fab)'2 anti-OE-coated cells. Thus, in comparative studies on phagocytosis, monocytes ingested an average of 52% of IgG coated red cells, 32% of red cells coated with My 43 bi-specific antibodies, and 0% of red cells coated with anti-β2 microglobulin antibodies. Accordingly, a binding agent having an antigen binding region specific for FcαR and an antigen binding region specific for an epitope on a target cells, e.g., a red blood cell, efficiently promotes phagocytosis of the target cells coated with the binding agent.

Another function triggered by cross-linking of receptor molecules is generation of superoxide. The U-937 monocyte-like cell line constitutes a useful model with which to study this function, because it has the capacity to produce large amounts of superoxide if cultured with IFN-γ (Anderson et al. (1986) *J. Biol. Chem.* 261:12856). Whereas U-937 cells obtained from ATCC and grown under standard conditions did not have ability to bind IgA, a U-937 subline originally from ATCC but grown for approximately 2 years (U-937-α) became capable of binding IgA after culture at low cell density with IFN-γ. The U-937α subline also bound more My 43 after IFN-γ treatment than U-937 from ATCC. In parallel with the receptor expression studies, these lines were compared for ability to generate superoxide in response to an IgG or IgA stimulus. In these studies IgA and IgG were complexed by binding to tissue culture plates before presentation to U-937 cells because it was found that IgA in solution bound to U-937 cells too weakly to effectively promote a response. Despite this multivalent presentation, only the U-937-α were triggered by IgA, whereas both populations responded to IgG.

Thus, immunization of mice with monocytes produced a monoclonal antibody, My 43, which triggers receptor mediated effector cell functions, e.g., phagocytosis of targeted cells, and production of superoxide anion. Furthermore, binding of mAb to the cell surface receptor is of greater avidity than that of soluble IgA.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. An antibody or fragment thereof comprising (a) an antigen binding region specific for a human Fcα receptor (FcαR) on an effector cell, and (b) a second antibody or antigen binding fragment thereof specific for a target antigen.

2. The antibody or fragment thereof of claim 1, wherein the target antigen is a tumor antigen.

3. The antibody or fragment thereof of claim 2, wherein the tumor antigen is an antigen from a cancer cell selected from the group of cancers consisiting of ovarian cancer, breast cancer, testicular cancer, prostate cancer, leukemia, and lymphoma.

4. The antibody or fragment thereof of claim 1, wherein the target antigen is an antigen on an auto-antibody producing cell.

5. The antibody or fragment thereof of claim 1, wherein the target antigen is an antigen from a microorganism.

6. The antibody or fragment thereof of claim 5, wherein the microorganism is a bacteria.

7. The antibody or fragment thereof of claim 5, wherein the microorganism is a virus.

8. The antibody or fragment thereof of claim 5, wherein the microorganism is a parasite.

9. The antibody or fragment thereof of claim 5, wherein the target antigen is a soluble antigen.

* * * * *